United States Patent [19]

Eshhar et al.

[11] Patent Number: 5,766,861
[45] Date of Patent: Jun. 16, 1998

[54] METHOD FOR SCREENING CATALYTIC NON-ENZYME POLYPEPTIDES AND PROTEINS

[75] Inventors: Zelig Eshhar, Rehovot; Bernard S. Green, Kvutsat; Dan S. Tawfik, Jerusalem, all of Israel

[73] Assignees: Yeda Research and Development Company Ltd., Rehovot; Yissum Research and Development Co. of the Hebrew University of Jerusalem, Jerusalem, both of Israel

[21] Appl. No.: 481,277

[22] PCT Filed: Jan. 12, 1994

[86] PCT No.: PCT/US94/00424

§ 371 Date: Aug. 22, 1995

§ 102(e) Date: Aug. 22, 1995

[87] PCT Pub. No.: WO94/16332

PCT Pub. Date: Jul. 21, 1994

[30] Foreign Application Priority Data

Jan. 13, 1993 [IL] Israel ......................... 104384

[51] Int. Cl.$^6$ ................................. G01N 33/573
[52] U.S. Cl. .................. 435/7.4; 435/7.1; 435/7.6; 435/188.5
[58] Field of Search ................. 435/7.1, 7.4, 7.6, 435/188.5

[56] References Cited

PUBLICATIONS

Rezaee, M. et al. (1987) Int. J. Cancer 40, 823–829.
Proceedings of the National Academy of Sciences, vol. 90, issued 15 Jan., 1993, Tawfik et al., "catElisa: A facile general route to catalytic antibodies", pp. 373–377, see entire article.
Ann. Rev. Biochem., vol. 61, issued 1992, Benkovic, "Catalytic Antibodies", pp. 29–54, especially pp. 44–45.
Analytic Biochemistry, vol. 202, issued 1992, Tawfik et al., "Detection of Catalytic Monoclonal Antibodies", pp. 35–39, see especially p. 39.
J. Am. Chem. Soc., vol. 114, issued 1992, Gong et al., "A Chromogenic Assay for Screening Large Antibody Libraries", pp. 1486–1487, see entire article.

*Primary Examiner*—Charles Patterson, Jr.
*Attorney, Agent, or Firm*—Browdy and Neimark

[57] ABSTRACT

A method for screening or detection of a non-enzyme catalytic polypeptide or protein for the conversion of a substrate S to a product P is provided, in which a preparation containing the potential catalyst is contacted with the substrate S immobilized to a support and the immobilized product P obtained is detected, preferably by immunoassay. The method is preferably used for the screening of hybridoma supernatants for catalytic monoclonal antibodies that catalyze acyl transfer reactions, e.g., hydrolysis or aminolysis, condensation reactions and resolution of enantiomers.

14 Claims, 7 Drawing Sheets

TS ANALOG = HAPTEN (4)

CO-SUBSTRATE (10)   SOLID-PHASE SUBSTRATE (11)

10a, BzOMe, X = CH₃;
10b, BzOtF, X = CH₂CF₃;
10c, BzOCn, X = CH₂CH₂CN;
10d, BzONSu, X = —N(succinimidyl)

PRODUCT (12)

FIG. 7B

TRANSITION STATE ANALOGS = HAPTENS 13
14
15

METHOD FOR SCREENING CATALYTIC NON-ENZYME POLYPEPTIDES AND PROTEINS

This application is a 371 of PCT/US 94/00424 Jan. 12, 1994.

FIELD AND BACKGROUND OF THE INVENTION

The present invention relates to the direct screening of hybridoma supernatants or other potential sources of catalysts for catalytic activity, and more particularly to a method for screening or detection of non-enzyme catalytic polypeptides and proteins, including catalytic antibodies.

One of the important goals of biotechnology is the ability to produce catalysts for any desired chemical reaction. This has many far-reaching applications in chemistry, biology and medicine. Many approaches towards this goal have been explored including site-directed modification of existing enzymes, microbial induction of new enzymes, totally synthetic peptides, and synthetic organic substances. Although fascinating and illuminating with regard to catalysis in general, none of these routes have provided a reliable, generally applicable technique for obtaining "tailor-made" catalysts.

The ability of catalytic antibodies to be tailor-made to a predesigned substrate, combined with rate enhancement and turnover, has led to the most intriguing enzyme mimics described thus far (1–3). Catalytic antibodies are elicited against a hapten, typically, a stable synthetic analog of the transition state (TS) of the catalyzed reaction. The repertoire resulting after immunization is immortalized as hybridomas (4), which are then screened to select those clones producing monoclonal antibodies that bind the hapten. The direct screening of culture supernatants of these hybridomas for antibody catalysis was heretofore not possible due to relatively high background reaction, the generally low catalytic efficiency of antibodies, and contaminating enzymes that catalyze the same reaction (5). Therefore, to detect catalytic activity, large quantities (usually from ascites fluid) of purified monoclonal antibodies are needed. Only a few, and occasionally none, of the dozens of clones that bind a hapten are catalytic; it is therefore widely recognized that these inefficient and labor-intensive procedures must be replaced by rapid and direct screening procedures (2, 3, 6–8). Novel, non-hybridoma, methodologies, such as combinatorial variable-region cloning in phage (9, 10) were also used to generate antibodies. Yet, as noted (11), future applications of these methodologies for obtaining catalytic antibodies depend upon appropriate screening. Gong et al. (28) proposed recently a chromogenic assay for screening large antibody libraries but the approach is both limited to hydrolysis reactions and includes labile ester groups which give strong background signals and, as has been shown (5), this disadvantage practically restricts the utility of such approaches.

There are several variations in approaches to elicit catalytic antibodies but the overall technique is as follows: The reaction which is to be catalyzed is analyzed in terms of the mechanism believed to be involved; this entails a depiction of the species which must be stabilized for the reaction to be catalyzed. Typically, this species is an unisolable transient state (the transition state or a high energy intermediate) which lies along the reaction pathway from reactant to product. Next, one or more stable chemical substances which mimic the stereoelectronic structure of the transient state are designed and synthesized. These substances are then used as haptens to elicit monoclonal antibodies (MABs) and various tests are made on each of the many (1000 or more) resulting hybridomas in order to ascertain which should be further studied. This initial screening method generally involves an ELISA assay to those MABs that are most tightly bound to the hapten (or transition state analog, TSA). These selected hybridoma cultures are then expanded and larger amounts of antibody are produced in order to determine whether any of these antibodies can catalyze the desired reaction. There are many controls that are required to ensure that no adventitious catalysts (e.g. enzyme impurities) are responsible for the observed catalysis. This approach or variations thereof have, as mentioned above, provided catalytic monoclonal antibodies (catMABs) which catalyze a relatively large number (more than 30) of specific chemical reactions (1–3).

It is clear from the above that there are, aside from the many techniques and protocols that must be mastered or learned, two basic problems in the successful production of catMABs: 1) the design and synthesis of the hapten which is used; 2) the initial screening of the hybridoma supernatants in order to select those cells which will be further studied.

The conventional approach for selection of clones, i.e., tight-binding to the immunizing hapten, is intrinsically flawed because it restricts the choice only to those MABs that bind the synthetic analog of the transition state and not any of the true transition states which exist along the reaction pathway. Also, it fails in allowing one to fully exploit the incredible diversity of the immune system and obtain MABs which may be poor binders to the TSA but which may be excellent catalysts. Finally, the conventional approach is very time-consuming and wasteful in energy and materials in that many individual hybridomas must be expanded and the many resulting antibodies must be purified and tested downstream from the initial selection. It has long been recognized that it would be far more effective and useful if one could directly screen for catalysis at the initial hybridoma supernatant stage. Indeed, this would be a breakthrough with significant wide-ranging ramifications in providing better catMABs more rapidly and efficiently.

We have solved this problem according to the present invention and developed a simple, efficient and effective direct screening for catalysis method.

SUMMARY OF THE INVENTION

Figure 1:
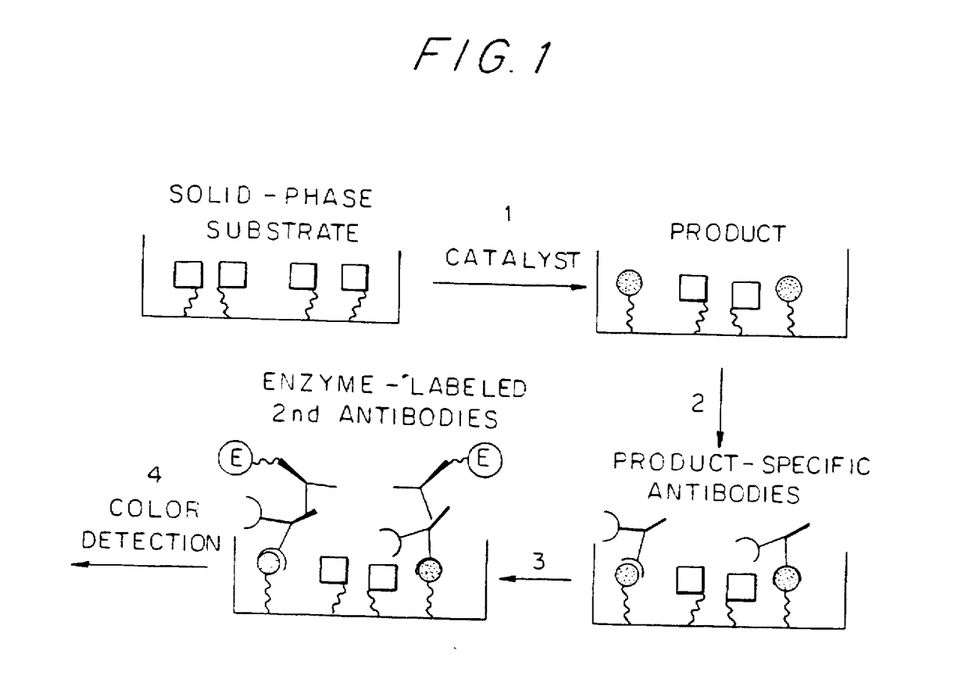
FIG. 1 depicts a schematic presentation of the method of the invention employing ELISA for detection of the bound antibody molecules.

Analysis of the unique problems involved in direct screening of hybridoma supernatants for antibody-mediated catalysis (5) led us to an assay involving, as a critical component, an immobilized "solid-phase" substrate, for example, a substrate-protein conjugate immobilized on microtiter plates. Antibody-catalyzed conversion of any "solid-phase" substrate to a product is then detected by any immunoassay, e.g., ELISA, using binding, anti-product P antibodies (FIG. 1).

According to the present invention, a method for screening or detection of non-enzyme catalytic polypeptides or proteins suitable for conversion of a substrate S to a product P is provided, said method comprising:
 i. immobilizing said substrate S to a support;
 ii. contacting a preparation comprising a potential catalytic polypeptide or protein with the immobilized substrate S, thus converting the substrate S completely or partially to a product P, which remains immobilized to the support;

iii. detecting the immobilized product P molecules with antibodies specific to said product P; and iv. detecting the product P-bound antibody molecules, the formation of product P at a rate and amount significantly higher than in a control reaction indicating the presence of said catalytic polypeptide or protein in the screened preparation.

The non-enzyme catalytic polypeptides or proteins that can be screened or detected by the method of the invention include, but are not limited to, natural and genetically-engineered antibodies, fragments thereof or single chain antibodies, and synthetic polypeptides or polymers of amino acids. In a preferred embodiment, the catalytic protein is a monoclonal antibody, preferably raised against a hapten which is a stable synthetic analog of the transition state of the catalyzed reaction, and direct screening is carried out in hybridoma supernatants. In another embodiment, combinatorial polypeptide libraries are screened for catalytic functional polypeptides.

Examples of reactions to be catalyzed are any acyl transfer reactions, e.g., hydrolysis or aminolysis, such as cleavage of a peptide bond and other cleavage reactions; condensation reactions, e.g., amide formation and Diels-Alder reaction; isomerization; resolution of enantiomers by selective reaction of one enantiomer or diastereoisomer; hydrolysis of phosphates, e.g., of tri- and diphosphates to monophosphates, and the like.

DESCRIPTION OF THE DRAWINGS

FIG. 9 illustrates the binding activity of polyclonal serum antibodies of a mouse immunized with 15-KLH. Five Balb/c mice were immunized with 15-KLH (50 μg/mouse emulsified in complete Freund's adjuvant (CFA)). After 14 days a boost was administered (50 μg/mouse in incomplete Freund's adjuvant (IFA)). Serum taken 10 days later was diluted in PBS (1:500–1:10,000) and assayed, by ELISA, for binding to 15-BSA, ●, 12-BSA, ▲, and BSA, □ (conjugates, 1 μg/ml in PBS, were used for coating). The results are of serum taken from mouse #3 that exhibited the highest titer. Competitive inhibition of binding to 15-BSA was observed in the presence of free, unconjugated 15 (15-N-glycylmethyl amide), 5 μM, ○, (and, >95% inhibition at 0.1 mM). Binding to 15-BSA was inhibited in the presence of product (12) as well, yet with a significantly lower affinity (e.g., 12, $I_{C50}$=2 mM, at 1:2,500 serum dilution).

DESCRIPTION OF THE PREFERRED EMBODIMENTS

The assay of the present invention for direct screening or detection of non-enzyme catalytic polypeptides or proteins involves a substrate S immmmobilized to a support, e.g., microtiter plates.

The non-enzyme catalytic polypeptides or protein to be detected or screened according to the invention may be monoclonal antibodies, single-chain antibodies, recombinant antibodies, fragments of antibodies, synthetic polypeptides and amino acid polymers, and the like. The assay is particularly useful for screening directly hybridoma supernatants for catalytic monoclonal antibodies, and combinatorial libraries, in which a functional polypeptide, e.g., a functional Fv, has to be selected out of millions of possibilities.

The substrate S is totally or partially converted to product P by the non-enzyme catalytic polypeptide or protein present in the preparation being screened, e.g., hybridoma supernatants obtained by fusion of cells of an animal immunized with a hapten corresponding to a stable synthetic analog of the transition state of the catalyzed reaction $S \geq P$, conjugated to a protein. In one example carried out according to the invention, the substrate is the p-nitrobenzyl ester 1a, the product is the carboxylic acid 3 and the antibodies are elicited against the transition state analog hapten 4 (FIG. 1).

Figures 7A, 7B:
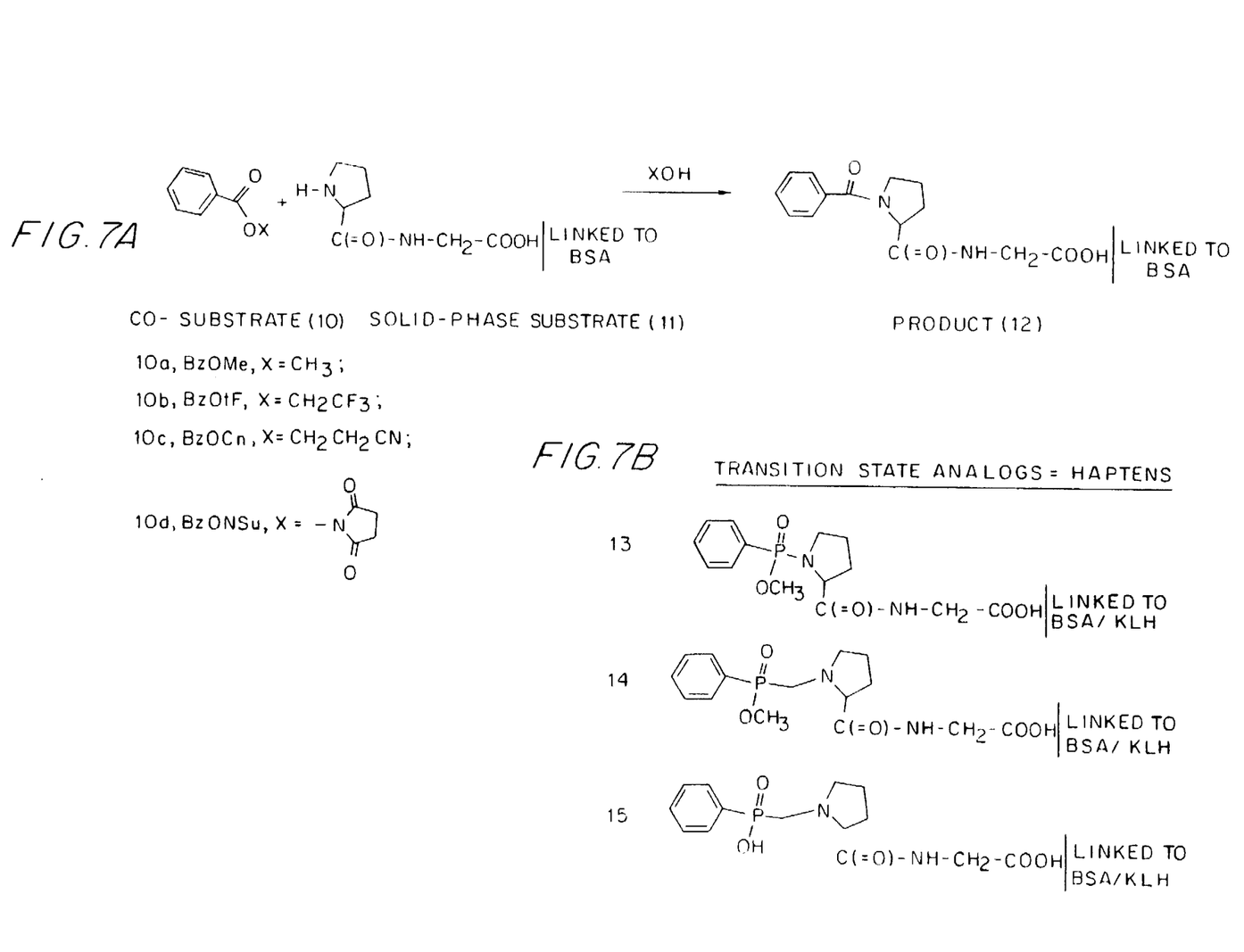
FIGS. 7A–B depict the chemical structures of (FIG. 7A) the substrate 11 and the co-substrates 10a–d, the amide product 12 resulting from their condensation, and (FIG. 7B) the transition state analogs haptens 13, 14 and 15. All of these substances were linked to a carrier protein (BSA or KLH) via the carboxyl group; the protein conjugates appear in the text as, for example, 11-BSA.

In a condensation reaction only one of the reagents will be immobilized to the support. The reaction with the co-substrate is catalyzed by the preparation containing the potential catalytic polypeptide or protein thus leading to product P, which remains immobilized to the support and is detected with specific antibodies. In one example carried out according to the invention, the solid-phase amine substrate conjugated to BSA 11 is reacted with the ester co-substrate 10, the amide product 12 remains immobilized to the support. The antibodies are elicited against a transition state analog hapten 13, 14 or 15 (FIG. 7).

The molecules of product P remain immobilized on the support and can be detected by any suitable immunoassay, e.g., ELISA, radioimmunoassay (RIA), chemiluminescence immunoassay (CIA), fluorescence immunoassay, using binding specific anti-product antibodies.

The presence of the catalytic polypeptide or protein in the tested preparation is established in all cases when product P is formed at a rate and amount significantly higher than in any of the control reactions, that are carried out with: (a) the immobilized substrate S alone; or (b) the immobilized substrate S in the presence of a non-relevant protein/ antibody; or (c) the immobilized substrate S alone or together with a non-relevant protein/antibody but omitting the anti-product P specific antibodies of step (iii).

FIG. 1 depicts the assay of the invention when conventional ELISA is used to detect the product. First the product molecules immobilized on the support are detected by anti-product specific antibodies, such as polyclonal antibodies raised in rabbits against the product P, and the bound antibody molecules are detected by enzyme-labeled second antibodies. We have designated the assay using ELISA as catELISA. Employing catELISA, we were able to rapidly screen thousands of hybridoma clones elicited against a phosphonate TS analog to detect catalytic cleavage of the corresponding p-nitrobenzyl ester.

A variety of antibody-catalyzed hydrolytic and other cleavage reactions as well as associative and condensation reactions are envisaged by the invention. Thus, substrate S may be an immobilized ester conjugated to a carrier protein, e.g., bovine serum albumin (BSA) or keyhole limpet hemocyanin (KLH), via the acid or the alcohol residue, and the resulting acid or alcohol product P thus remains immobilized on the support, detection in step (iii) is carried out with antibodies specific to the acid or alcohol product P, the bound specific antibodies being detected in step (iv) by immunoassay.

The substrate S may be an amide conjugated to a carrier protein via the acid or the amine residue, and the resulting acid or amine product P thus remains immobilized on the support, detection in step (iii) is carried out with antibodies specific to the acid or amine product P, the bound specific antibodies being detected in step (iv) by immunoassay.

The substrate S may also be a single enantiomer or a single diastereoisomer and the screened catalytic polypeptide or protein will catalyze the resolution of said compounds to afford the desired enantiomer or diastereomer.

The substrate S may also be a polypeptide that is cleaved to a smaller peptide. For example, it may be a toxin that is cleaved and converted to a non-toxic molecule. Thus, catalytic antibodies that cleave toxins may be useful in medicine, e.g., for treatment of septic shock.

The substrate S may also be an amine, e.g. an amino acid 11 linked to a carrier protein via the carboxylic residue and the co-substrate is an ester 10, and the product P is the resulting amide that remains immobilized to the support, and detection in step (iii) is carried out with antibodies specific to the amide. Other associative and condensation reactions are also envisaged by the invention.

Figure 2:
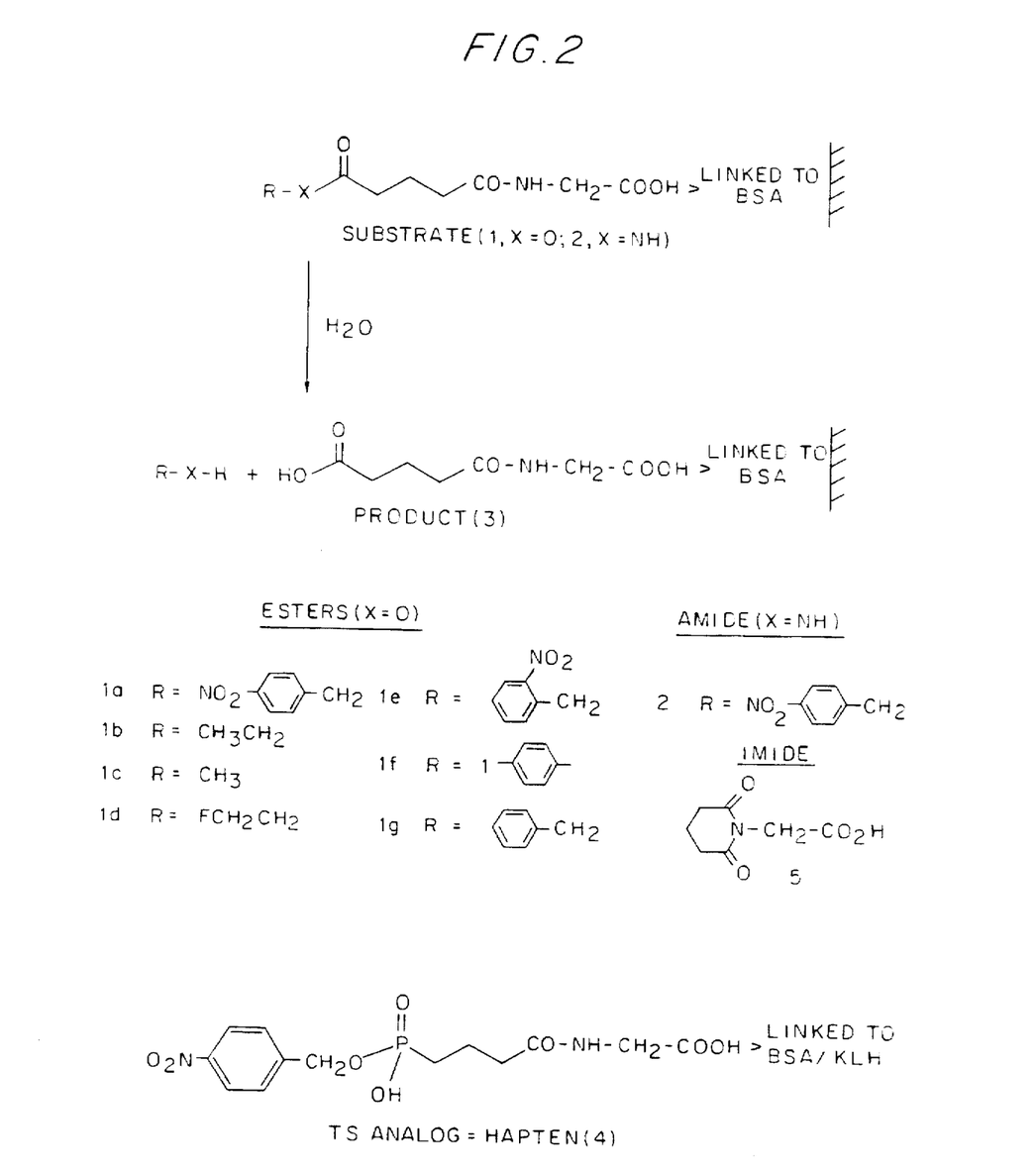
FIG. 2 depicts the chemical structures of substrates, 1a–g, 2 and 5, the product of their hydrolysis, acid 3, and the hapten, 4. All of these substances were linked to a carrier protein (BSA or KLH) via the carboxyl group; the protein conjugates appear in the text as, for example, 1a-BSA.

The systems presented here were designed to study, among others, a variety of antibody-catalyzed acyl-transfer, e.g., hydrolytic, reactions. Cleavage of immobilized esters 1a–g, amides (e.g. 2), or imide 5 leaves the carboxylic acid product 3 bound to the solid phase (FIG. 2). Anti-product 3 polyclonal antibodies which do not cross-react with any of the substrate conjugates were used for detection.

Figure 3A:
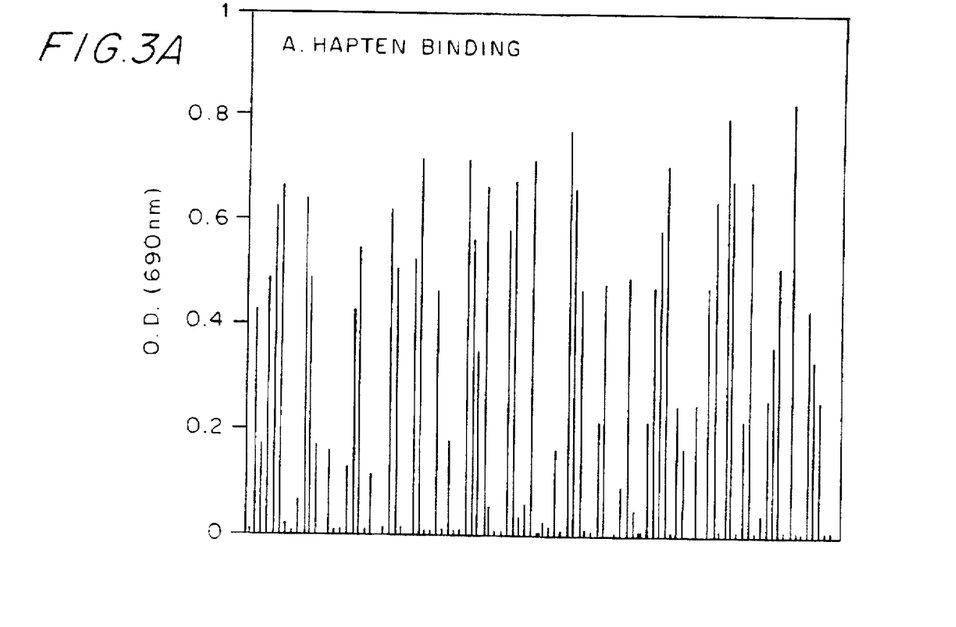
FIGS. 3A–B show the results of screening of one microculture plate (96 hybrid clones, each represented by a bar) for hapten binding antibodies (panel A), and for catalytic activity (panel B). Hapten binding (A) was determined by ELISA using 50 μl of hybridoma supernatants in microtiter plates coated with 4-BSA (1 μg/ml); the assay (B) was performed with the p-nitrobenzyl ester substrate, 1a-BSA (see Materials and Methods). The last 3 bars are controls: L, lipase (OD $A_{690}$=1.0); Tris-buffered saline (TBS), pH 8.3; and S, 0.1M sodium carbonate. Two catalytic antibody clones, D2.3 (indicated as clone 3 in FIG. 3B) and D2.4 (indicated as clone 4 in FIG. 3B) that exhibit significant product formation over the control (e.g., TBS), were identified from this plate.
Figure 3B:
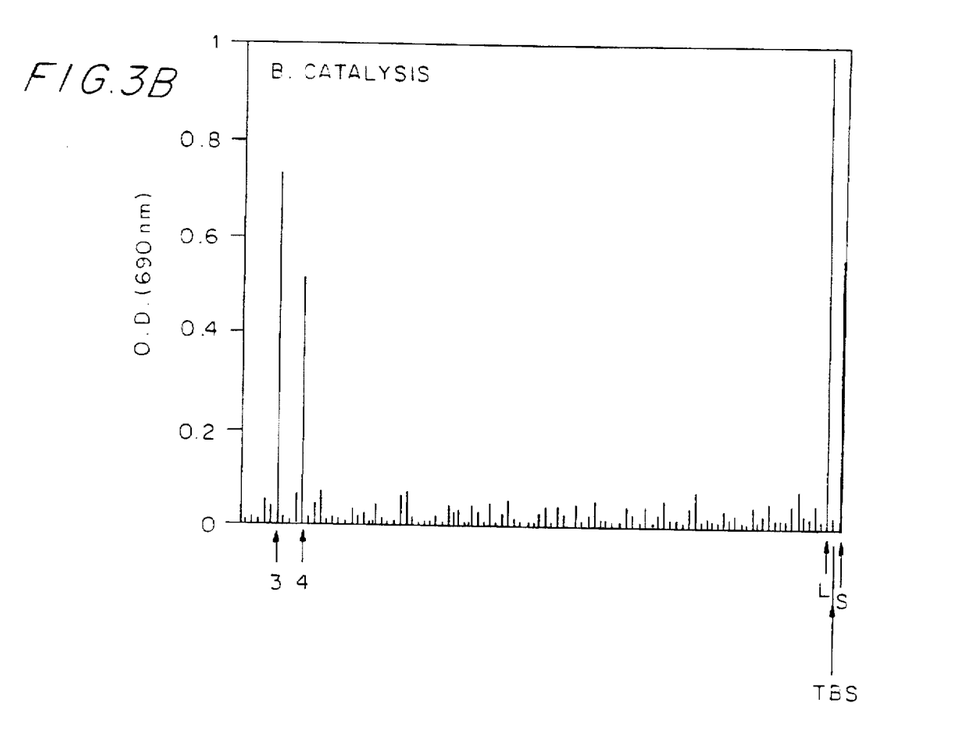

To first establish the feasibility of the catELISA system we studied the enzyme- or base-catalyzed hydrolysis of esters 1a–d and imide 5. The BSA conjugates of these substrates, coated on microtiter plates, were treated with mild base (sodium carbonate, 0.1M, pH 10.9) or pancreatic lipase for various time periods. Formation of the resulting acid product 3 was then determined by conventional ELISA using the rabbit anti-3 antibodies followed by peroxidase-linked, anti-rabbit immunoglobulin antibodies. No signal is observed with amides, e.g., 2, which represent substrates that are stable to base or to lipase-catalyzed hydrolysis. As expected, imide 5 is hydrolyzed in the presence of sodium carbonate ($t_{1/2}$=45 min compared with 90 min for the methyl ester, 1c) but not by the lipase. The rates of hydrolysis of esters 1a–d in the presence of various dilutions of lipase reach a maximum with increasing enzyme concentration (FIG. 3). This is ascribed to the very small amount of substrate that is coated on the solid phase (ca. 10–50 pmole per well). The kinetics of the enzyme- and base-catalyzed reactions shows that as little as 5% of substrate conversion to product can be measured. The activity of less than 0.01 unit of lipase can be readily detected even with ester substrates such as 1a–d, which are far from optimal structures for this enzyme. These and additional experiments indicated that catELISA is sensitive and selective and can be applied for the direct screening of catalytic antibodies in hybridoma supernatants.

EXAMPLES

Materials and Methods

Preparation of Substrates and Haptens. All of the synthesized substances were purified to homogeneity (judged by thin layer chromatography and NMR) by crystallization or silica column chromatography. Structures were confirmed by NMR and mass spectrum; satisfactory elemental analyses were obtained for all crystalline compounds. Esters 1a, 1b, 1e and amide 2 (FIG. 2) were prepared by the following procedures: (i) allowing the corresponding alcohol or amine to react with glutaric anhydride in the presence of a base (1b, ethanol, sodium ethoxide, reflux; 1a and 1e, p-nitrobenzyl alcohol or o-nitrobenzyl alcohol, 1,8-diazabicyclo[5.4.0]-undecane (DBU); 2, p-nitrobenzyl-amine; $Et_3N$); (ii) coupling of t-butyl glycinate by using N,N'-dicyclohexylcarbodiimide (DCC); and (iii) removal of the t-butyl ester in the presence of trifluoroacetic acid (TFA). The methyl ester 1c was prepared by esterification of N-glutaryl-O-benzylglycine with diazomethane and the 2-fluoroethyl ester 1d by esterification with 2-fluoroethanol in the presence of thionyl chloride; removal of the benzyl esters by catalytic hydrogenation gave the products. Imide 5 was prepared by heating glutaric anhydride and glycine benzyl ester in the presence of acetic anhydride; the benzyl ester was then removed by catalytic hydrogenation. Substrates were conjugated to bovine serum albumin (BSA) or keyhole limpet hemocyanin (KLH) via their N-hydroxysuccinimide esters.

For the preparation of the protein conjugates of carboxylic acid 3 (product), the corresponding p-iodophenyl ester 1f was synthesized: t-butyl glycinate was added to glutaric anhydride, and the resulting mono acid was then coupled to p-iodophenol using DCC. After removal of the t-butyl ester the resulting 1f was coupled to protein (via the N-hydroxysuccinimide ester) and then hydrolyzed (0.1M $Na_2CO_3$, 3 hours) to give the carboxylic acid 3-BSA and 3-KLH. The synthesis and conjugation of phosphonate 4 was carried out as described in Ref. 12.

BSA conjugates of prolylglicine (11-BSA) were prepared as follows: (i) conjugation of a protected prolyl peptide, Fmoc—Pro—Gly—OH, via a NSu ester, to BSA. (ii) After extensive dialysis, against 6M urea and PBS, the Fmoc (fluorenyl methoxycarbonyl) protection was removed in situ on the protein in the presence of piperidine (5%, in 1:3, THF:0.1M $NaHCO_3$). Hapten densities (Hd) were determined by measuring absorbance of the conjugated Fmoc moiety ($\epsilon_{300\ nm}=5,300\ M^{-1}cm^{-1}$) before deprotection. Conjugates having 20–30 prolyl-glycyl residues per molecule BSA were used for catELISA.

12-BSA and 12-KLH were prepared by the reaction of Bz-ProGly-ONSu (Bz=benzoyl; NSu=N-hydroxy succinimide ester) 10 μmol, in 200 μL DMF) with BSA or KLH (10 mg or 5 mg, respectively, in 0.1M $NaHCO_3$).

catELISA. Anti-product 3 antibodies were prepared by immunizing rabbits with the KLH conjugate of carboxylic product 3 (hapten density=17 per molecule; 100 μg per rabbit, emulsified in complete Freund's adjuvant (CFA), followed by a boost, 14 days later, in incomplete Freund's adjuvant (IFA)). The sera taken after 24 days exhibited high binding affinity to the product (3-BSA, hapten density=10, titer=1:5,000) and minimal crossreactivity (<10% at 1:5,000 dilution) with the various substrate conjugates (1a–d, 2 and 5-BSA). For the catELISA, microtiter plates (Nunc, Maxisorb) were coated with 1a-BSA (hapten density=15, 1.0 μg/ml, 1 hour) and then blocked with BSA (1 mg/ml, 0.5 hour). The hybridoma supernatants (50 μl) were incubated for 3 hours and the plates were then washed with phosphate buffered saline (PBS, 10 mM sodium phosphate, 0.14M NaCl, pH 7.4)+0.04% Tween. The rabbit anti-product 3 serum was then added (1:5,000 dilution in PBS+0.04% Tween, 1 hour). After washings and incubation with peroxidase-linked mouse anti-rabbit immunoglobulin antibodies (Jackson, Immuno Research, diluted 1:5,000 in PBS) the substrate, 2,2'-azinobis(3-ethyl benzthiazoline sulfonic acid) (ATBS), was added and the absorbance at 690 nm was measured. Base (0.1M sodium carbonate, pH 10.9) or lipase (porcine pancreatic, crude extract, Sigma L-3126, 50 μg/ml) were used as positive standards for hydrolysis.

Anti-product 12 antibodies were prepared by immunizing rabbits with 12-KLH (100 μg/Rabbit, emulsified in CFA), followed by a boost 14 days later (100 μg/Rabbit in IFA). The sera taken after 14 days exhibited high binding affinity to 12-BSA (titer>1:10,000) and no cross reactivity with 11-BSA.

For catELISA, microtiter plates were coated with 11-BSA (10–20 μg/mL, overnight, 4° C.). The plates were washed twice with PBS/T and then with PBS. The supernatant, sera, or a buffer (40 mM PBS pH 7.4) was incubated in the presence of a benzoyl ester, Bz-OX (10a–d; 0.01–5 mM), for various periods of time (10 min–24 hrs). The plates were then washed with PBS/T and the anti-12 rabbit polyclonal sera (diluted 1:4,000 in PBS/T) was added. After further washings and incubation with peroxidase-linked mouse anti-rabbit antibodies (Jackson, diluted 1:5,000 in PBS) the substrate (ATBS) was added and the absorbance at 690 nm measured.

The conditions for screening supernatants by catELISA were optimized so that the background signal in the absence of a catalyst is minimized and the positive signal observed after complete cleavage with sodium carbonate or lipase is maximal. Thus, different concentrations of conjugates were used for coating the plates for each of the substrates (0.1–5 μg/ml). Optimal results were obtained with substrate-BSA conjugates having hapten densities of 10–20.

EXAMPLE 1. Hybridomas and Monoclonal Antibodies.

Balb/c mice were immunized (foot pad injection) with the hapten conjugate 4-KLH (hapten density=16, 50 μg per mouse in CFA) (FIG. 2). After 14 days, a boost was administered (50 μg per mouse in IFA) and two more injections (i.p., 50 μg per mouse) were given 4 and 3 days before fusion (45 days from immunization) with NSO myeloma cells.

A short immunization protocol was used with the substrate conjugate 2-KLH (FIG. 2) (hapten density=16); 3 Balb/c and 3 C57BL mice were immunized (50 μg per mouse in CFA). After 17 days a boost in IFA was given and 3 days later the draining lymph node cells were fused with NSO myeloma cells.

Two weeks after fusions, the supernatants of the resulting hybrid clones were screened by catELISA. Positive clones were propagated as ascites in Balb/c mice. The antibodies were purified by staphylococcal protein A (Pharmacia) affinity chromatography and dialyzed against Tris-buffered saline [TBS; 50 mM tris(hydroxymethyl)amino-methane/ 0.14M NaCl], pH 8.25 or 9.0. Homogeneity of the purified antibodies was judged by SDS-PAGE, which yielded only heavy and light chains under reducing conditions, with Coomassie blue staining. Fusions, growth of hybridoma cell lines, immunoassays and production of monoclonal antibodies in ascites fluid, were carried out as described in Ref. 13 and 14.

The catalytic activity of the protein A-purified antibodies was determined by measuring the appearance of p-nitrobenzyl alcohol and the disappearance of substrate 1a in homogeneous solutions, using HPLC for detection and quantification. The substrate, in dimethyl sulfoxide, was added to the antibody in 50 mM TBS, pH 8.25 or 9.0 (final organic solvent <1%). Aliquots of the reaction mixtures were quenched (acetonitrile+0.1% TFA) and analyzed by HPLC (RP-8, 100×5 column; 27:73, water/acetonitrile+

0.1% TFA; flow 1.0 ml/min; detection by absorbance at 277 nm; retention times for substrate 1a, 6.9 min, and for the product, p-nitrobenzyl alcohol, 4.1 min).

The concentration of the antibodies (Abo) was determined by active site titration with 4 (as 4-N-benzylamide). The uncatalyzed rate of hydrolysis ($k_{uncat}$) of ester 1a, determined by initial rates analysis and extrapolated to zero buffer concentration, is 2.8×10−5 min−1 at pH 8.25. The activity of the catalytic antibodies with the o-nitrobenzyl and benzyl esters (1e and 1g, respectively; 1 mM) were studied by HPLC; no rate enhancement was observed in the presence of the purified antibodies (0.3–5 µM).

To generate catalytic antibodies, the phosphonate hapten 4 was used primarily because of the demonstrated ability of phosphonoesters to mimic the tetrahedral, negatively charged, TS/intermediate of ester hydrolysis and to elicit ester-hydrolyzing antibodies (1). Spleen cells from a mouse immunized with the p-nitrobenzyl phosphonoester conjugate, 4-KLH, were fused with myeloma NSO cells and the resulting 1570 hybrid clones (970 of which were hapten-binding clones) were assayed by catELISA for their ability to induce hydrolysis of the substrate ester 1a (FIG. 2). Representative data from the screening of the initial hybridoma supernatants are given in FIG. 3; as can be seen, although dozens of clones bind the phosphonate hapten, only two scored positive in the catELISA. Altogether, 9 clones that catalyze the cleavage of ester 1a were identified.

Figure 4:
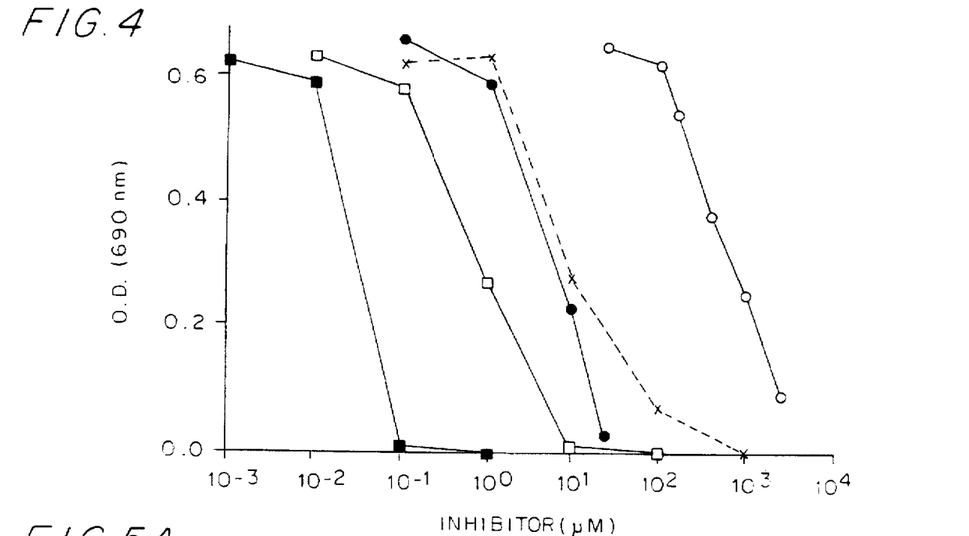
FIG. 4 shows the inhibition pattern of esterolytic activity of D2.3 determined by the assay of the invention. Antibody D2.3 (protein A-purified preparation, 20 nM in TBS pH 8.25) was incubated on microtiter plates coated with 1a-BSA in the presence of various dilutions of the following: filled squares, phosphonate hapten 4 (as 4-N-benzylamide); empty squares, a "short" hapten (mono-p-nitrobenzyl methyl phosphonate); filled circles, amide substrate 2 (2-N-methylamide); and empty circles, p-nitrobenzyl alcohol. Dashed line, inhibition of the signal was also observed when the added rabbit sera containing anti-product antibodies (applied after incubation with the catalytic antibody) contained product 3 (3-N-methylamide).

Control experiments provided conclusive evidence that the catELISA signal observed in the presence of the hybridoma supernatants is indeed due to antibody-catalyzed hydrolysis of the p-nitrobenzyl ester substrate, 1a. None of the selected clones gave a signal in catELISA when esters other than the p-nitrobenzyl ester (1b–d in FIG. 2) were used as substrates (e.g., antibody D2.3 on 1b, not shown). The affinity pattern of the catalytic site (FIG. 4) is as expected for an antibody elicited against hapten 4, i.e., hapten 4>"short" hapten>amide substrate>p-nitrobenzyl alcohol (product). Indeed, the same order of affinity was observed when the inhibition of binding of these antibodies to the hapten-BSA conjugate was measured by ordinary competitive inhibition immunoassay (CIEIA; for a similar analysis, see ref. 13). Product inhibition, pH-activity profiles, substrate specificity, and other properties that characterize the overall quality of these antibodies as catalysts were all conveniently determined by catELISA prior to the purification of the antibodies (data not shown).

Figure 5A:
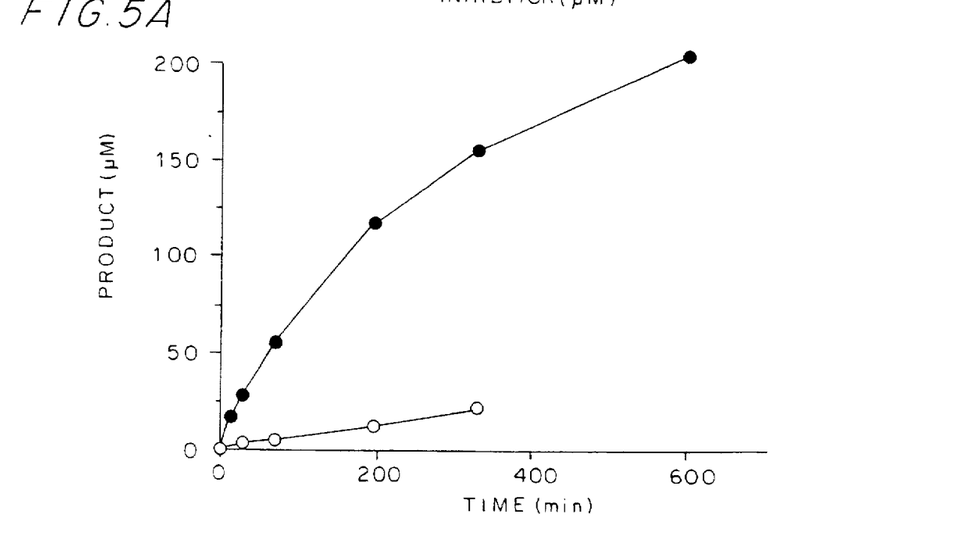
FIG. 5A shows hydrolysis of the unconjugated ester substrate 1a (0.3 mM) by monoclonal antibody D2.3 (0.3 μM) (filled circles) determined by HPLC; activity is inhibited in the presence of hapten 4 (4-N-benzylamide, 1.0 μM) (empty circles).
Figure 5B:
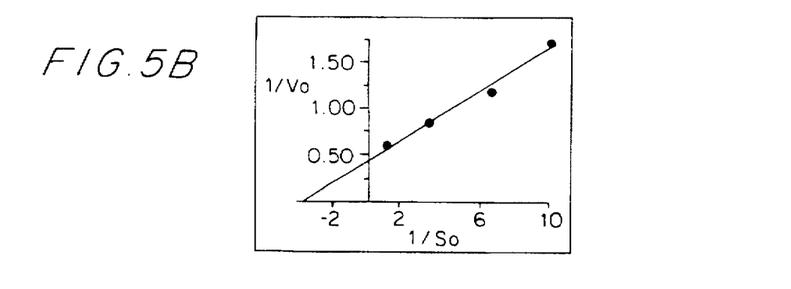
FIG. 5B shows kinetic parameters determined by a Lineweaver-Burk analysis performed with 1a at pH 8.25 ($Ab_o$=0.3 μM, $1/S_o$ is given in $mM^{-1}$ and $1/v_o$ in min. $\mu M^{-1}$).

Purified antibodies from ascites fluid were assayed by HPLC for their ability to catalyze the hydrolysis of the free, unconjugated p-nitrobenzyl ester 1a (FIGS. 5A–5B). The results confirmed the catELISA selection.

The identification, by catELISA, of clones exhibiting relatively low rate accelerations (e.g., antibody clone D2.1:$k_{cat}/k_{uncat}$ about 700, at pH 9.0), underlines the sensitivity and selectivity of the catELISA. Neither "background" (i.e., uncatalyzed) hydrolysis of the ester substrate nor the presence of enzymes in the hybridoma supernatants interfered. Solid-phase esters, e.g., 1a, were found to be stable in the presence of most esterases that hydrolyze the soluble, unconjugated esters (e.g., porcine liver esterase, acetylcholinesterase); these enzymes catalyze the hydrolysis of the same ester substrate in solution (i.e., not immobilized to a solid-phase). Moreover, we have examined other biological fluids (e.g., human and mouse sera, mouse ascites, bacteria growth media, etc.) that are known to contain esterases, by catELISA on ester 1a-BSA (and on additional substrates). We have found that in none of these cases a "background" signal that is higher than the signal observed after incubation with a buffer (e.g., PBS pH 7.4), was observed, and that, catalytic antibodies secreted to all these media could be efficiently detected.

Using a "solid phase" substrate for the detection of catalytic antibodies affords two additional distinct advantages: the catalytic antibody has increased affinity for the substrate that includes the protein carrier structure (i.e., lower Km values) and the relatively low substrate concentration ensures that pseudo-first order conditions are maintained (Km>>So). It was suggested (5) that these two factors directly increase the ability to detect antibody-mediated catalysis. The signal observed due to antibody catalyzed hydrolysis of ester 1a ($\Delta P_{cat}$, or $v_{o\ cat}$) over the background, i.e., under the same conditions in the presence of a non-catalytic antibody ($\Delta P_{uncat}$, or $v_{o\ uncat}$) is significantly increased by catELISA (FIG. 6).

Figure 6A:
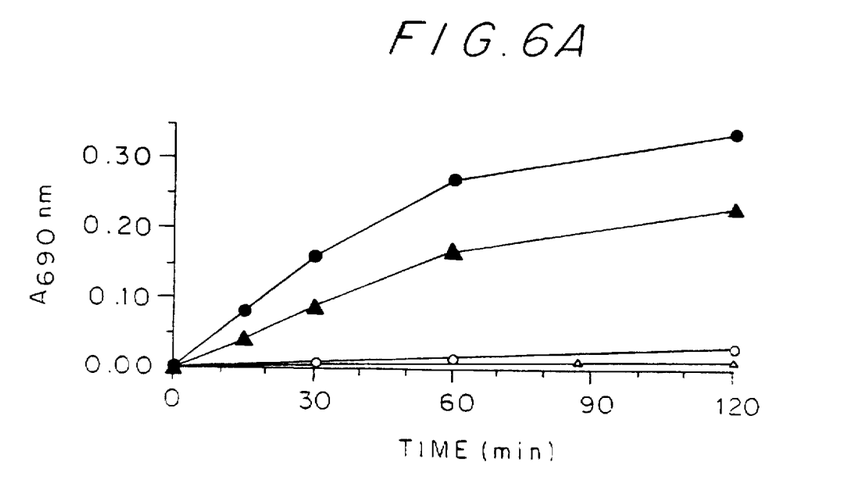
FIGS. 6A–B show rates of hydrolysis of ester 1a by: catalytic antibody D2.5 (full symbols), and in the presence of a non-catalytic antibody as a control (DEl, empty symbols) assayed by: Panel A, catELISA on microtiter plates coated with 1a-BSA using culture supernatants of D2.5 (~7 nM; ●,▲) or DEl (~7 nM; ○, △); and by, Panel B, HPLC using 1a, unconjugated (0.3 mM), and protein A purified preparations of antibody D2.5 (3.5 μM; ●, ▲) or DEl (3.5 μM; ○, △). The supernatants of, or purified, antibodies were dialyzed beforehand against 50 mM TBS pH 8.3 (▲, △) or pH 9.0 (●, ○).
Figure 6B:
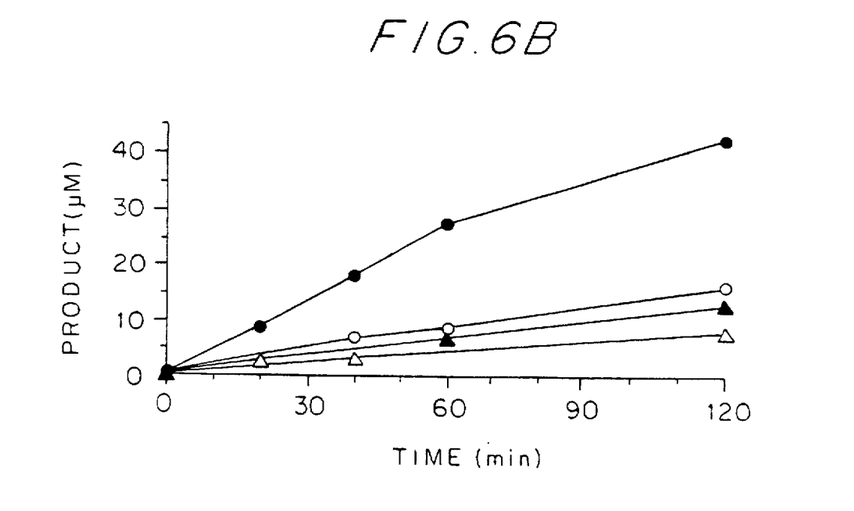

For example, catELISA with 1a-BSA gives a clear significant signal, both at pH 8.25 and 9.0, using hybridoma supernatants containing antibody D2.5 (FIG. 6A, $v_{o\ cat}/v_{o\ uncat}$=50 and 80). The rate enhancement observed by conventional assay with the free, unconjugated, 1a, (using a protein A purified preparation and HPLC for detection and quantification of the released product) is orders of magnitude smaller (FIG. 6B, $v_{o\ cat}/v_{o\ uncat}$ at pH 8.25˜1.0, and at pH 9.0, ˜2.5) even though the concentration of the antibody used is at least 50 fold higher than in the unpurified supernatants used for the catELISA. This difference can be attributed to the lower Km and So of the solid-phase 1a-BSA, as well as to the higher sensitivity of the ELISA detection.

Thus, solid-phase substrates are favourable for the detection of antibody-mediated catalysis, regardless of the method used to detect the product of the reaction. In addition to the immunodetection described in these studies, alternative detection techniques may be used, e.g., detection of the soluble product that is released to the supernatant (p-nitrobenzyl alcohol, in the above example) by using radioactively labeled products, fluorescence, absorbance, etc.

Another antibody, D2.3, exemplifies a truly efficient, enzyme-like catalyst (FIG. 5; $k_{cat}$=7.35 min$^{-1}$, Km=0.28 mM, at pH 8.25), exhibiting not only significant rate enhancement ($k_{cat}/k_{uncat}$=2.6×10$^5$) with an un-activated ester substrate, but also multiple turnovers (>1,000). Turnover, i.e., the ability of a single binding site to repetitively process substrate molecules, is often found to be limited by severe product inhibition in catalytic antibodies (for example, see refs. 15–20). In spite of the presence of the nitrophenyl group (15), the p-nitrobenzyl alcohol product binds to antibody D2.3 with low enough affinity (Kd=52 µM) to allow efficient turnover (FIG. 5). D2.3 is also characterized by its notable substrate specificity; it recognizes not only the p-nitrobenzyl moiety (i.e., no catalysis is observed with the benzyl or o-nitrobenzyl esters 1g and 1e) but also the acyl part of the substrate: the $k_{cat}/k_m$ value with p-nitrobenzyl acetate was estimated to be less than 10 sec$^{-1}$M$^{-1}$, compared to 440 with N-(O-p-nitrobenzylglutaryl) glycine (1a). Direct screening, therefore, not only can save the effort of handling hundreds of hapten-binding noncatalytic clones, but it also should increase the variety and quality of the selected catalytic antibodies.

EXAMPLE 2

Additional fusions were screened for catalytic activity by catELISA. Different strains of mice were immunized with 4-KLH, and with 2-KLH, and were screened for hydrolysis of the respective ester substrate 1a-BSA and amide substrate, 2-BSA. Immunizations, fusions, and screenings were all performed as described in Example 1 and in Materials and Methods; results obtained from all these experiments are summarized in Table 1.

The catalytically active antibody clones identified by catELISA were propagated in ascites and purified on protein A column as in Example 1. An ordinary assay, with ester 1a (soluble), using HPLC for detection and quantification of the product, confirmed the results obtained by catELISA.

TABLE I

| Immunization | | Mice | No. of clones | | |
| --- | --- | --- | --- | --- | --- |
| Antigen | injections/period | No./Strain | total | hapten binding | catalytic |
| 4-KLH | 4/45 days | 2/Balb/c | 1570 | 970 | 9 |
| " | 5/125 days | 1/Balb/c | 860 | n.d. | 6 |
| " | 2/21 days | 2/Balb/c | 564 | 32 | 1 |
| " | 4/44 days | 1/SJL | | 162 | 10 |
| " | 2/21 days | 4/NZW | | 252 | 3 |

These results further demonstrate the ability of catELISA to rapidly screen for antibody-mediated catalytic activity under conditions in which: (i) the antibody is present in very low concentrations, (ii) enzyme contaminants, that may catalyze the reaction, are present.

EXAMPLE 3

The approach of catELISA is not only facile but also general: it is not limited by type of reaction or substrate. An additional example is the condensation reaction of an ester and an amine to yield an amide, involving an associative, bimolecular reaction, to compare with the previous example of hydrolysis of an ester, or an amide, which is a dissociative, unimolecular reaction. Acylation of proline, rather than of any other amino acid, is an intriguing target for antibody catalysis because all the enzymes that are known to catalyze peptide synthesis (e.g., subtilisin, chemotrypsin) are inactive towards proline substrates.

The detection system was based on a solid-phase substrate, i.e., prolylglycyl conjugated to BSA and immobilized on to microtiter plates (11-BSA); the co-substrate, i.e., an ester of benzoic acid (10), that is present in the mobile phase, is added together with the examined antibody or buffer solution (FIG. 7A). Nucleophilic substitution of the benzoate ester by the amino group of the proline results in the formation of immobilized benzoyl-prolylglycyl, 12-BSA, and the release of the respective alcohol. Antiproduct 12 polyclonal rabbit antibodies, that do not crossreact with the prolyglycyl substrate (11-BSA), or with benzoyl-BSA, were used for detection.

Figure 8:
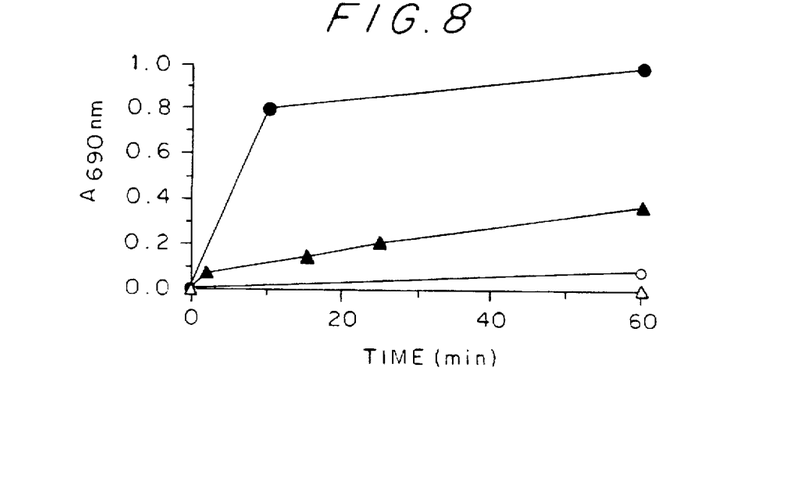
FIG. 8 depicts benzoylation of prolylglycyl followed by catELISA. Microtiter plates were coated with 11-BSA (full symbols; Hapten density (Hd)=28, 10 μg/ml, overnight, 4° C.), or BSA (open symbols) and Bz-ONSu (10d) in 40 mM PBS pH 7.4 was added (1 mM, ●, ○, or 0.1 mM, ▲,△) for various periods of time (0–60 min). The plates were washed with PBS+0.04% Tween (PBS/T) and the anti-12 rabbit polyclonal sera (diluted 1:4,000 in PBS/T) was added. After further washings and incubation with peroxidase-linked mouse anti-rabbit antibodies (Jackson, diluted 1:5,000 in PBS) the substrate (ATBS) was added and the absorbance at 690 nm was measured.

To demonstrate the feasibility of this catELISA system we have studied the in-situ acylation of solid phase prolyl glycyl (11-BSA) by benzoyl-NSu (N-hydroxy succinimide ester) (10d). N-hydroxy succinimide esters are highly reactive with amines and are routinely used for peptide synthesis in aqueous media. The formation of solid phase benzoyl-prolyl glycyl (12-BSA) was detected using anti-12 rabbit polyclonal antibodies (FIG. 8). As shown, the signal observed is time and concentration dependent. Furthermore, N-hydroxy succinimide esters are not selective, thus they react with both prolyl amino groups and with any other amino groups that are present in the reaction, e.g., ε-amino groups of lysine residues of the BSA. Nevertheless, detection by catELISA proved to be specific to the benzoylation of prolyglycyl; the signal observed due the formation of benzoyl-BSA is practically insignificant (FIG. 8).

Other esters of benzoic acid, e.g., methyl, trifluoroethyl, or cyanoethyl (10a, b and c, respectively), that are not as reactive as N-hydroxy succinimide esters, did not yield the product, benzoyl-prolyl glycyl (12-BSA), even after longer incubations (e.e., 5 mM, for 24 hrs, at room temperature). These esters are to be added in the presence of supernatants of antibodies elicited against appropriate transition state analogs to identify antibodies that catalyze the benzoylation of prolylglycyl-BSA as described above.

Figure 9:
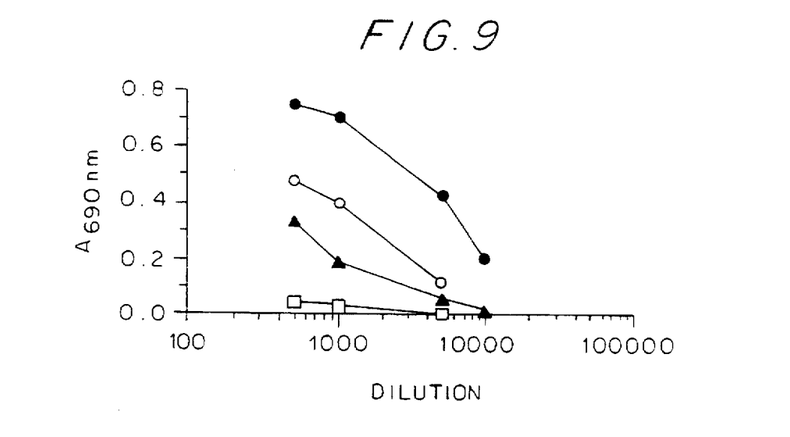
Figure 10:
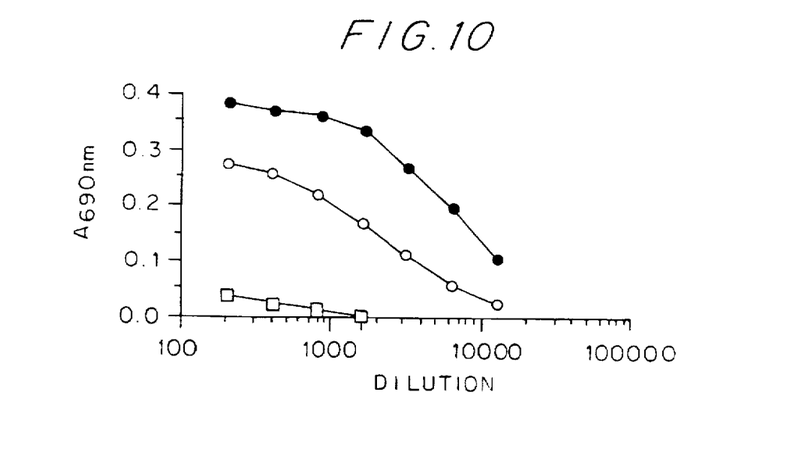
FIG. 10 illustrates the binding activity of polyclonal serum antibodies of a mouse immunized with 13-KLH. Four Balb/c mice were immunized with 13-KLH (50 μg/mouse emulsified in CFA). After 14 days a boost was administered (50 μg/mouse in IFA). Serum taken 10 days later was diluted in PBS (1:200–1:15,000) and assayed, by ELISA, for binding to 13-BSA, ●, 12-BSA, ○, and BSA, □ (conjugates, 1 μg/ml in PBS, were used for coating). The results are of serum taken from mouse #4 that exhibited the highest titer.

Transition state analogs for the amidation reaction described above were designed and synthesized (FIG. 7B), and linked to carrier proteins (BSA or KLH). Immunization of Balb/c mice with the KLH conjugates of haptens 13–15 resulted in a high and specific binding response (FIG. 9 and FIG. 10). Hybrid clones obtained by fusion of lymphocytes taken from these mice with NSO myeloma cells were screened for binding to the hapten (i.e., to the hapten-BSA conjugate) and for catalysis of amidation of prolyglycyl in the presence of methyl or cyanoethyl benzoate (10a and 10c, respectively; 5 mM, for 24 hrs at room temperature). Positive antibody clones that catalyze the benzoylation of substrate 11 to give amide product 12 are identified and caracterized as described in Example 1.

REFERENCES

1. Lerner, R. A., Benkovic, S. J. & Schultz, P. G. (1991) Science 252:659–667.
2. Catalytic Antibodies, Ciba Foundation Symposium No. 159 (1991) (Wiley, N.Y.).
3. Green, B. S. & Tawfik, D. S. (1989) Trends Biotechnol. 7:304–310.
4. Kohler, G. & Milstein, C. (1975) Nature (London) 256:495.
5. Tawfik, D. S., Green, B. S. & Eshhar, Z. (1992) Anal. Biochem. 202:35–39.
6. Schultz, P. G. (1989) Angew. Chem. Int. Ed. Eng. 28:1283–1444.
7. Lerner, R. A. & Benkovic, S. J. (1988) Bioessays 9:107.
8. Schultz, P. G., Lerner, R. A. & Benkovic, S. J. (1990) Chem. Eng. News 68 (22):26–40.
9. Winter, G. & Milstein, C. (1991) Nature (London) 349:293–299.
10. Huse, W. D., Sastry, L., Iverson, S., Kang, A. S., Alting-Mees, M., Burton, D. R., Benkovic, S. J. & Lerner, R. A. (1989) Science 246:1275–1281.
11. Iverson, S. A., Sastry, L., Huse, W. D., Sorge, J. A., Benkovic, S. J. & Lerner, R. A. (1989) Cold Spring Harbour Symposia on Quantitative Biology 54:273–281.
12. Tawfik, D. S., Eshhar, Z. & Green, B. S. (1992) Phosphorus and Sulfur, in press.
13. Tawfik, D. S., Zemel, R. R., Arad-Yellin, R., Green, B. S. & Eshhar, Z. (1990) Biochemistry 29:9916–9921.
14. Eshhar, Z. (1985) in Hybridomas in Biotechnology and Medicine, ed. Springer, T., (Plenum Press, N.Y.) pp 1–41.
15. Benkovic, S. J., Adams, J. A., Borders, C. L. Jr., Janda, K. D. & Lerner, R. A. (1990) Science 250:1135–1139.
16. Martin, M. T., Napper, A. D., Schultz, P. G. & Rees, A. R. (1991) Biochemistry 30:9757–9761.
17. Janda, K. D. et al. (1991) J. Amer. Chem. Soc. 113:291–297.
18. Iverson, B. L., Cameron, K. E., Jahangiri, G. K. & Pasternak, D. S. (1990) J. Amer. Chem. Soc. 112:5320–5323.
19. Cochran, A. G. & Schultz, P. G. (1990) Science 249:781–783.
20. Jacobsen, J. R., Prudent, J. R., Kochersperger, L., Yonkovich, S. & Schultz, P. G. (1992) Science 256:365–376.
21. Lerner, R. A. (1984) Adv. Immunol. 36:1–44.
22. Pollack, S. J., Hsuin, P. & Schultz, P. G. (1989) J. Am. Chem. Soc. 111:5960–5961.

23. Paul, S., Volle, D. J., Beach, C. M., Johnson, D. R., Powell, M. J. & Massey, R. J. (1989) Science 244:1158–1162.
24. Blackburn, G. M., Kingsbury, G., Jayaweera, S. & Burton, D. R., in ref. 2, pp. 211–226.
25. Paul, S., Johnson, D. R. & Massey, R. J., in ref. 2, pp. 156–173.
26. Jencks, W. P. (1989) Catalysis in Chemistry and Enzymology (McGraw-Hill, N.Y.) p. 288.
27. Green, B. S. (1989) Advances in Biotechnological Processes, ed. Mizrachi, A., 7:359–393.
28. Gong, B., S. A. Lesley and P. G. Schultz (1992) J. Am. Chem. Soc. 114:1486–1487.

We claim:

1. A method for screening or detection of a catalytic polypeptide or protein suitable for the conversion of a substrate S to a product P, said method comprising:

i. immobilizing said substrate S to a support;

ii. contacting a preparation comprising a potential catalytic polypeptide or protein with the immobilized substrate S, thus converting the substrate S completely or partially to a product P, which remains immobilized to the support;

iii. detecting the immobilized product P molecules with antibodies specific to said product P; and iv. detecting the product P-bound antibody molecules, the formation of product P at a rate and amount significantly higher than in a control reaction indicating the presence of said catalytic polypeptide or protein in the screened preparation.

2. A method according to claim 1, wherein the catalytic proteins to be screened or detected are antibodies, single chain antibodies, fragments of antibodies, synthetic polypeptides or synethetic amino acid polymers.

3. A method according to claim 1, for the direct screening of hybridoma supernatants for catalytic monoclonal antibodies, wherein said preparation comprising a potential catalytic polypeptide is a hybridoma supernatant.

4. A method according to claim 3, wherein said hybridoma supernatants are those containing monoclonal antibodies elicited against a stable synthetic analog of the transition state of a catalyzed reaction S≧P, and catalytic monoclonal antibodies are detected by formation of product P at a rate significantly higher than in a control reaction carried out with irrelevant antibodies.

5. A method according to claim 1, for the direct screening of combinatorial polypeptide libraries for catalytic functional polypeptide, wherein said preparation comprising a potential catalytic polypeptide is a member of a combinatorial polypeptide library.

6. A method according to claim 1, wherein the substrate S is linked directly to a protein and the substrate S-protein conjugate is immobilized on microtiter plates.

7. A method according to claim 1, wherein the substrate S is linked to a protein via a linker and the substrate-linker-protein conjugate is immobilized on microtiter plates.

8. A method according to claim 1, for the screening or detection of polypeptides or proteins that catalyze the hydrolysis of an immobilized ester S, the resulting immobilized acid or alcohol product P being detected in step (iii) by anti-P specific antibodies, that are then detected in step (iv) by immunoassay.

9. A method according to claim 1, for the screening or detection of polypeptides or proteins that catalyze the cleavage of an immobilized amide S, the resulting immobilized amine or acid product P being detected in step (iii) by anti-P specific antibodies that are then detected in step (iv) by immunoassay.

10. A method according to claim 1, for the screening or detection of polypeptides or proteins that catalyze a reaction selected from the group consisting of: (a) resolution of an enantiomer or diastereomer; (b) cleavage of a large peptide S to a small peptide P; and (c) cleavage of a toxin to a less toxic or non-toxic substance.

11. A method according to claim 1, for the screening or detection of polypeptides or proteins that catalyze the synthesis of an amide from an immobilized amine substrate S and an ester co-substrate, the resulting immobilized amide product P being detected in step (iii) with anti-P specific antibodies, that are then detected in step (iv) by immunoassay.

12. A method according to claim 1, wherein the anti-product P specific antibodies are polyclonal antibodies.

13. A method according to any one of claim 1, wherein the product P-bound antibody molecules in step (iv) are detected by ELISA.

14. A method according to claim 1, wherein said substrate S is non-polymeric.

* * * * *